United States Patent [19]

Kimura et al.

[11] Patent Number: 4,997,850

[45] Date of Patent: Mar. 5, 1991

[54] TREATING AGENT FOR OSTEROARTHRITIS

[75] Inventors: Fumihiko Kimura, Tokyo; Yutaka Mukaida, Iruma; Koju Watanabe, Sakado, all of Japan

[73] Assignee: Kureha Kagaku Kogyo Kabushiki Kaisha, Tokyo, Japan

[21] Appl. No.: 507,839

[22] Filed: Apr. 12, 1990

[30] Foreign Application Priority Data

Apr. 28, 1989 [JP] Japan .................. 1-110148
Feb. 15, 1990 [JP] Japan .................. 2-34065

[51] Int. Cl.$^5$ .................................. A61K 31/235
[52] U.S. Cl. ........................ 514/544; 514/699; 514/825
[58] Field of Search .............. 514/544, 699, 825

[56] References Cited

U.S. PATENT DOCUMENTS

| | | | |
|---|---|---|---|
| 4,248,892 | 2/1981 | Kanamoru et al. | 514/578 |
| 4,758,591 | 7/1988 | Takita et al. | 514/548 |
| 4,841,097 | 6/1989 | Noda et al. | 560/144 |

FOREIGN PATENT DOCUMENTS 55-51018  4/1980  Japan .
58-183619 5/1983  Japan .
59-196818 11/1984 Japan .

*Primary Examiner*—Shep K. Rose
*Attorney, Agent, or Firm*—Nixon & Vanderhye

[57] ABSTRACT

The present invention discloses a method for treating a patient suffering from osteoarthritis comprising administering a physiologically effective amount of pharmaceutical composition containing at least one compound, as an active ingredient, represented by the formula (I):

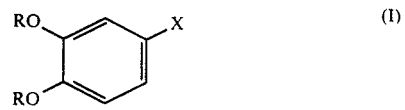

wherein R represents a hydrogen atom or an acyl group; X represents a CHO group, a COOH group, a physiologically acceptable salt thereof or a CH(OR')$_2$ group wherein R' represents an acyl group.

9 Claims, 5 Drawing Sheets

B = BLANK LPS(−)
C = CONTROL LPS(+)

TREATING AGENT FOR OSTEROARTHRITIS

BACKGROUND OF THE INVENTION

The present invention relates to treating agents for osteoarthritis, comprising as an active ingredient, a compound represented by the formula (I):

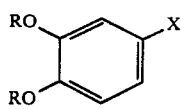

wherein R represents a hydrogen atom or an acyl group, X represents a CHO group, a COOH group or a physiologically acceptable salt thereof, or a CH(OR')$_2$ group wherein R' represents an acyl group.

As an arthrosis, rheumatiod arthritis, rheumatic fever and osteoarthritis have been popular so far and especially there were many patients suffering from rheumatiod arthritis or rheumatic fever and these two disorders have been studied since the two diseases were the main subject matter among arthrosis. However, recently, in proportion of an increase of aged people in the total population, patients suffering from a primary osteoarthritis due to a senescence of a joint, especially to a deformation of cartilage by detrition are increasing and accordingly the disease becomes a subject of watching by many physicians.

Up to now, among the compounds represented by the formula (I), 3,4-dialkanoyloxybenzylidene dialkanoate including 3,4-diacetoxybenzylidene diacetate (hereinafter referred to as "ACP"), 3,4-dialkanoyloxybenzaldehyde including 3,4-dihydroxybenzaldehyde (hereinafter referred to as "PAL") and 3,4-dialkanoyloxybenzoic acid including 3,4-dihydroxybenzoic acid (hereinafter referred to as "PAC") have been known effective as anti-inflammatory agents, treating agents for nephritis, anti-cancer agent and agents for suppressing fibrogenesis. For example, U.S. Pat. No. 4,758,591 discloses ACP as an anti-inflammatory agent, Japanese Patent Application (hereinafter referred to as "JP-A"), Laid-Open (KOKAI) No. 55-51,018 (1980) does PAL as an anti-cancer agent, JP-A, Laid-Open (KOKAI) No. 58-83,619 (1983) does PAL as an anti-inflammatory agent, JP-A, Laid-Open (KOKAI) No. 59-196,818 (1984) does PAL as an anti-nephritis agent and U.S. Pat. No. 4,248,892 does PAC as an anti-fibrogenesis agent.

Further, U.S. Pat. No. 4,758,591 describes that 3,4-dialkanoyloxybenzylidene dialkanoate including ACP, and PAL are appropriate agents treating inflammatory; rheumatic disease such as rheumatoid arthritis; and autoimmune diseases such as glomerular nephritis or systemic lupus erythematosus; since they exhibit suppressing activity of leukocyte migration, granuloma proliferation and adjuvant arthritis and further they are very low toxic to mammals including human. However, the above references do not say anything at all about osteoarthritis.

Osteoarthritis is a retroplasia occurred in a joint and there are a secondary one due to an congenital hypoplasia, trauma or other diseases and a primary one due to a retroplasia of joint cartilage. In general, osteoarthritis occurs mostly at a joint more or less supporting body weight. A secondary and congenital one are found frequently at a hip joint and a primary one due to senescences is found often at a joint of spine or a knee.

Osteoarthritis is sometimes classified as a rheumatic diseases in its broad meaning, but it is a different disease from so-called rheumatism such as rheumatoid arthritis and rheumatic fever. For example, a rheumatic fever is accompanied with a lesion in heart and a rheumatoid arthritis has an adhesion in the joint. However, osteoarthritis causes a deformation of cartilage of a joint but no adhesion in the joint nor a lesion in heart. Furthermore, rheumatoid arthritis is not limited to a joint having a load such as a knee joint or a hip joint and its pathopoiesis is often observed at a joint of hand or finger. Accordingly, osteoarthritis is different from rheumatism and should be classified separately from rheumatism.

Further, rheumatoid arthritis is a systemic disease and causes an inflammation in connective tissues and an administration of a conventional anti-inflammatory agent is a one of main treatments. In osteoarthritis, it also causes an inflammation in a synovial membrane but it is not a main lesion and accordingly simple administration of conventional anti-inflammatory agents does not give sufficient results for the treatment.

The present inventors have studied extensively to develop a pharmaceutical drug to treat osteoarthritis, which disease is gathering notice of many physicians since aging phenomena recently become remarkable throughout the advanced countries, and taking into their consideration a recent finding that interleukin 1 (hereinafter referred to as "IL-1") is noted as a joint cartilage destroying factor, they have created a concept that if they could develop a drug which is capable of suppressing a production or a release of IL-1 by macrophages, they would be able to attain the present invention.

Based on this concept, the inventors have studied earnestly and have found the facts that 3,4-dialkanoyloxybenzylidene dialkanoate including ACP, PAL, PAC and its physiologically acceptable salt have a strong activity to suppress a production and/or a release of IL-1. Further, they have also found the fact that the above compounds of the present invention can suppress a decomposition of cartilage matrix and a release of proteoglycan which is a main constituent of the cartilage, as its fragment. Based upon these supplemental findings, they have completed the present invention.

BRIEF EXPLANATION OF THE DRAWINGS

In FIGS. 1 and 2, each symbol *,  and * shows a difference under level of significance not higher than 5%, not higher than 1% and not higher than 0.1%, respectively.

SUMMARY OF THE INVENTION

Figure 1A:
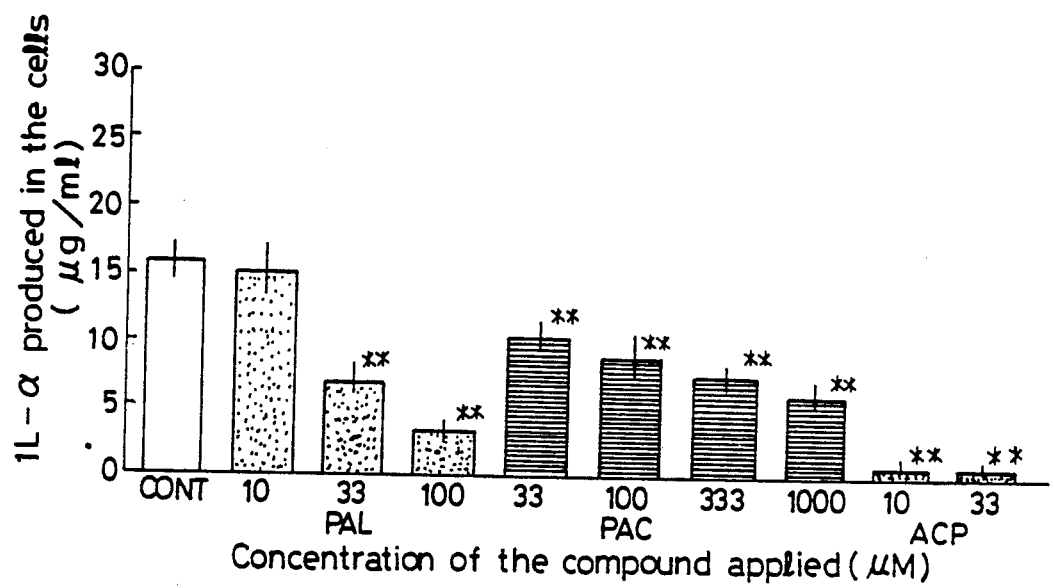
FIGS. 1(a) and 1(b) show the experimental results of inhibiting activities of ACP, PAL and PAC, on IL-1 production in human synovial cells. The values are shown in the form of a mean value ± standard error (n=3) on bar graphs.

An object of the present invention is to provide a method for treating a patient suffering from osteoarthritis comprising an administration of a physiologically effective amount of pharmaceutical composition containing, as an active ingredient, at least one compound represented by the formula (I):

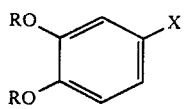

wherein R represents hydrogen atom or an acyl group, X represents a CHO group, a COOH group or physiologically acceptable salts thereof, or a $CH(OR')_2$ group wherein R' represented an acyl group.

DETAILED EXPLANATION OF THE PRESENT INVENTION

The present invention relates to a method of treating osteoarthritis patients, comprising an administration of a physiologically effective amount of pharmaceutical composition containing, as an active ingredient, at least one compound represented by the formula (I):

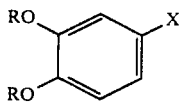

wherein R represents a hydrogen atom or an acyl group, X represents a CHO group, a COOH group or physiologically acceptable salts thereof, or a $CH(OR')_2$ group wherein R' represents an acyl group.

In the formula (I), R and R', Acyl groups, are represented by the formula:

respectively, wherein Y and Y' independently represent a linear or branched alkyl group having 1 to 18, preferably 1 to 7, more preferably 1 to 2 carbon atoms, or aromatic residue such as a phenyl group or an alkylphenyl group.

As the compounds represented by the formula (I), the following compounds can be exemplified:
3,4-diacetoxybenzylidene diacetate,
3,4-dipropionyloxybenzylidene dipropionate,
3,4-dibutyryloxybenzylidene dibutyrate,
3,4-didodecanoyloxybenzylidene didodecanoate,
3,4-ditetradecanoyloxybenzylidene ditetradecanoate,
3,4-dihexadecanoyloxybenzylidene dihexadecanoate,
3,4-dioctadecanoyloxybenzylidene dioctadecanoate,
3,4-diacetoxybenzylidene dioctadecanoate,
3,4-dioctadecanoyloxybenzylidene diacetate,
3,4-dibenzoyloxybenzylidene dibenzoate,
3,4-dihydroxybenzaldehyde,
3,4-diacetoxybenzaldehyde,
3,4-dioctadecanoyloxybenzaldehyde,
3,4-dibenzoyloxybenzaldehyde,
3,4-dihydroxybenzoic acid and its physiologically acceptable salts,
3,4-diacetoxybenzoic acid and its physiologically acceptable salts.

3,4-Dialkanoyloxybenzylidene dialkanoate including ACP is a compound represented by the formula (II):

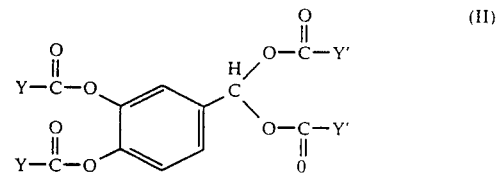

and its method of synthesis is described in U.S. Pat. No. 4,758,591 and is summarized as below:

(1) When Y and Y' are identical (Y=Y'), for example, PAL represented by the formula (III) is reacted with alkanoic acid anhydride represented by the formula (IV), in the presence of a mineral acid such as sulfuric acid, etc. as illustrated in the following reaction formula:

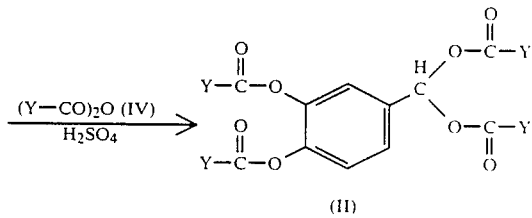

(2) When Y and Y' are not identical, the compound, for example, represented by the formula (V) is reacted with alkanoic acid anhydride represented by the formula (VI), in the presence of a mineral acid such as sulfuric acid, etc. as illustrated in the following reaction formula:

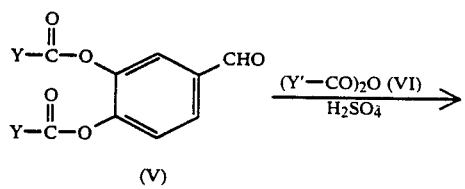

(V)

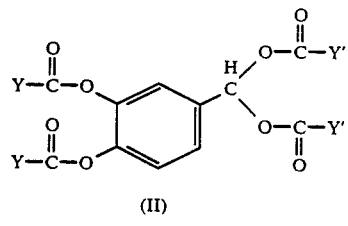

(II)

The synthesis of the compound represented by the formula (V) is performed, for example, PAL represented by the formula (III) reacting with alkanoic acid halide of the formula (VII), Y-COZ wherein Z represents a chlorine atom or a bromine atom, in the presence of triethylamine, pyridine, etc. in an inactive organic solvent such as benzene, dichloromethane, etc., as illustrated in the following reaction formula:

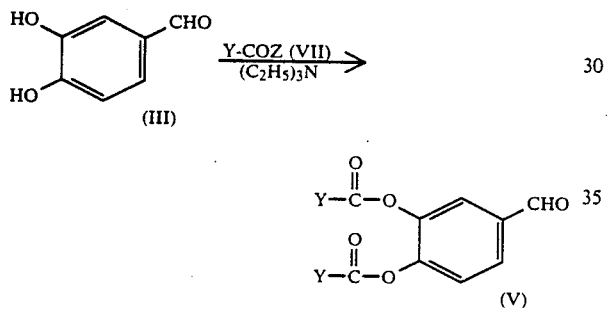

acid such as sulfuric acid etc., as illustrated in the following reaction formula:

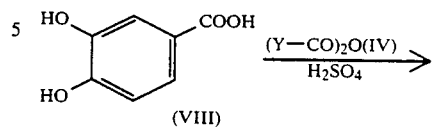

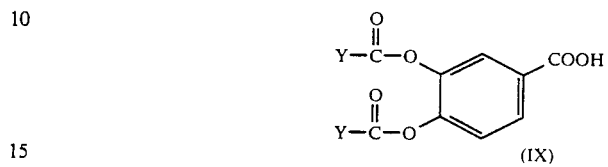

The toxicological and pharmacological features of the compound of the present invention are explained hereinafter.

(1) Acute Toxicity (i) Acute toxicity of ACP

ACP was administered orally or subcutaneously to mice and rats, male and female, their clinical sign was observed for seven days after the administration and each $LD_{50}$ was determined by the method calculating on the Litchfield-Wilcoxon figure.

For oral administration, a suspension of ACP dispersed in an aqueous solution of 0.5% methylcellulose and 0.4% Tween 80 (nonionic surfactant, manufactured by TOKYO KASEI, Co., Ltd.) was prepared and administered to the animals via a stomach sonde. For subcutaneous administration, a suspension of ACP dispersed in an aqueous physiological saline solution containing 0.5% of carboxymethyl cellulose sodium (hereinafter referred to as "CMC") was prepared and injected to the animals with a syringe. The results are shown in Table 1.

TABLE 1

| Route* Animal Tested | Oral | | | | Subcutaneous | | | |
|---|---|---|---|---|---|---|---|---|
| | CD-1/ Mouse | | Sprague- Dawley/Rat | | Jcl:ICR/ Mouse | | Jcl:Wistar/ Rat | |
| Sex | male | fem.* | male | fem.* | male | fem.* | male | fem.* |
| No. of Animals | 5 | 5 | 5 | 5 | 10 | 10 | 10 | 10 |
| $LD_{50}$ (g/kg) | >5 | >5 | >5 | >5 | >4 | >4 | >4 | >4 | fem.*: means female

PAC is a compound represented by the formula (VIII):

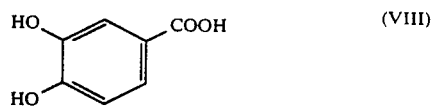

and as its physiologically acceptable salts, those with alkali metals such as sodium salt and potassium salt, those with alkaline earth metals such as calcium salt and ammonium salt can be exemplified.

3,4-Dialkanoyloxybenzoic acid represented by the formula (IX) can be prepared by reacting PAC represented by the formula (VIII) with alkanoic acid anhydride of the formula (IV) in the presence of a mineral Further, the acute toxicities ($LD_{50}$) of
3,4-di-n-propionyloxybenzylidene di-n-propionate,
3,4-di-n-dodecanoyloxybenzylidene di-n-dodecanoate,
3,4-di-n-octadecanoyloxybenzylidene di-n-octadecanoate,
3,4-dibenzoyloxybenzylidene dibenzoate,
3,4-di-n-butyryloxybenzylidene di-n-butyrate,
3,4-di-n-tetradecanoyloxybenzylidene di-n-tetradecanoate,
3,4-di-n-hexadecanoyloxybenzylidene di-n-hexadecanoate,
3,4-diactoxybenzylidene di-n-octadecanoate,
3,4-di-n-octadecanoyloxybenzyliden diacetate,
3,4-diacetoxybenzaldehyde,
3,4-di-n-octadecanoyloxybenzaldehyde,
3,4-dibenzoyloxybenzaldehyde and 3,4-diacetoxybenzoic acid and its sodium salt were also determined in the same manner and obtained the approximately same values.

(ii) Acute toxicity of PAL

PAL was administered orally or intraperitoneally to each of five female Jcl:ICR mice per group and their situation was observed for seven days after the administration and each $LD_{50}$ was determined by the method calculating on the Litchfield-Wilcoxon figure.

For oral administration, a suspension of PAL dispersed in an aqueous solution of 0.2% CMC was prepared (a part of PAL was dissolved in the solution) and administered to the animals via a stomach sonde. For intraperitoneal administration, a suspension of PAL dispersed in an aqueous physiological saline solution was prepared (a part of PAL was dissolved in the solution) and injected to the animals with a syringe. The results are shown in Table 2.

TABLE 2

| Route for Administration | $LD_{50}$ Value (mg/kg) |
| --- | --- |
| Oral | 1,503 |
| intraperitoneal | 404 |

(iii) Acute Toxicity of PAC

PAC was administered interperitoneally to each of five male mice per group and their clinical sign was observed for 8 days after the administration and obtained $LD_{50}$ value of not less than 400 mg/kg with the same method as item (ii) above. The same level of $LD_{50}$ value was also obtained for a sodium salt of PAC.

(2) Inhibition of a Production and Release of IL-1

(i) Inhibiting activity of ACP, PAL and PAC on IL-1 production in human synovial cells Human synovial membrane obtained at an operation was treated with collagenase to obtain synovial cells, which were subcultured several times and inoculated on a 12-well culture dish. On reaching to confluence, the cells were provided to the test described below. The synovial cells produce IL-1 but release only a little amount and accordingly are appropriate cells to study an inhibition or an acceleration of IL-1 intracellular production.

Figure 1B:
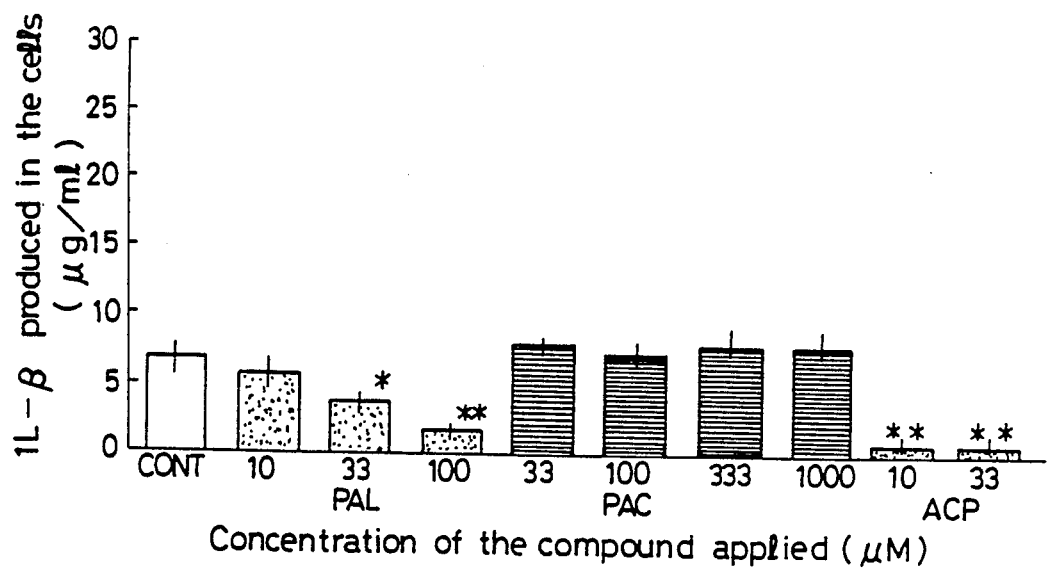

Each DMSO (dimethylsulfoxide) solution containing one of ACP, PAL and PAC separately in a concentration of 400 times that of the final test and DMSO solution not containing any of the compound as a control, were diluted to 40 times in its volume with a medium containing fetal bovine serum (hereinafter referred to as "FBS") [Ham Medium]. 100 $\mu$l of the diluted solution was added to each well and further, 800 $\mu$l of the medium [Ham] was added to each well. At the same time, 100 $\mu$l of the medium [Ham] containing tetradecanoylphorbol acetate (Hereinafter referred to as "TPA") and $Ca^{2+}$ ionophore A 23187 was added to the each well. The concentration of TPA and the ionophore in the medium were adjusted so that their final concentration in the well became 0.1 $\mu$g/ml and 0.2 $\mu$g/ml, respectively and a production of IL-1 was stimulated. Final volume of the liquid (medium) per well was 1 ml/well. After 40 hours of culture, liquid portion was removed from each well and 1 ml of a Ham medium was added to the remaining cells in each well. Freeze-thawing was repeated on the medium containing the cells several times to destroy all the cells in the medium and supernatants containing intracellular substances were obtained by centrifugation. IL-1$\alpha$ and IL-1$\beta$ in the supernatant were determined by ELISA method using a prescribed enzyme-antibody-complex (manufactured by OHTSUKA SEIYAKU, Co., Ltd.) as intracellular IL-1s. [Refer to ENSHO, vol. 8 (5) 409 (1988)]. The results are shown in FIGS. 1(a) and 1(b). As is clear from the FIGS. 10 $\mu$M of ACP and 33 $\mu$M of PAL show a strong inhibiting activity of both IL-1$\alpha$ and IL-1$\beta$ production, 33 $\mu$M of PAC shows an inhibiting activity of IL-1$\alpha$ only.

Figure 2A:
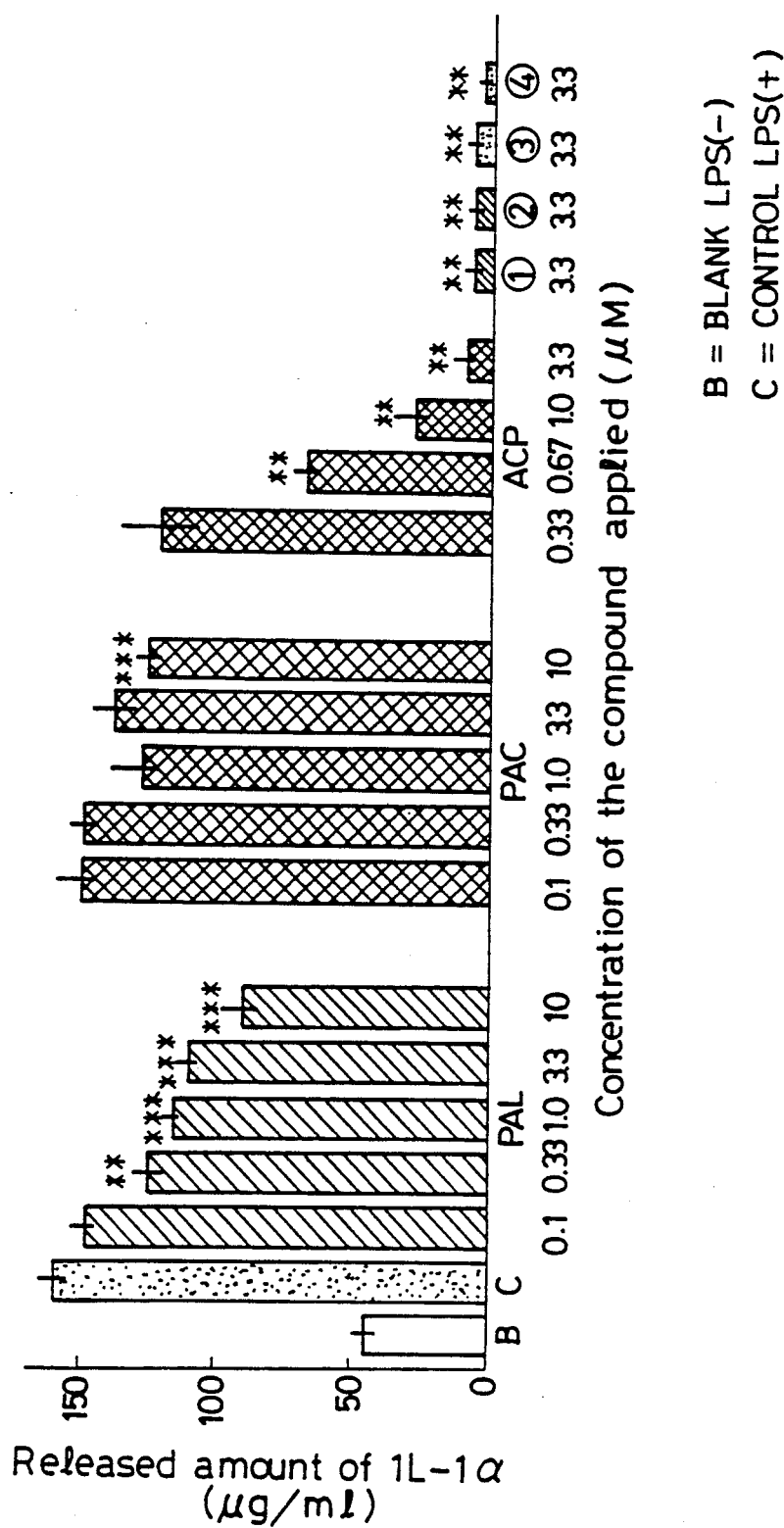
FIGS. 2(a) and 2(b) show the experimental results of the inhibiting effects of ACP, 3,4-di-n-propionyloxybenzylidene di-n-propionate, 3,4-di-n-dodecanoyloxybenzylidene di-n-dodecanoate, 3,4-di-n-octadecanoyloxybenzylidene di-n-octadecanoate, 3,4-dibenzoyloxybenzylidene dibenzoate, PAL and PAC on IL-1 production in human monocyte. The values are shown in the form of a mean value ± standard error (n=3) on bar graphs.
Figure 2B:
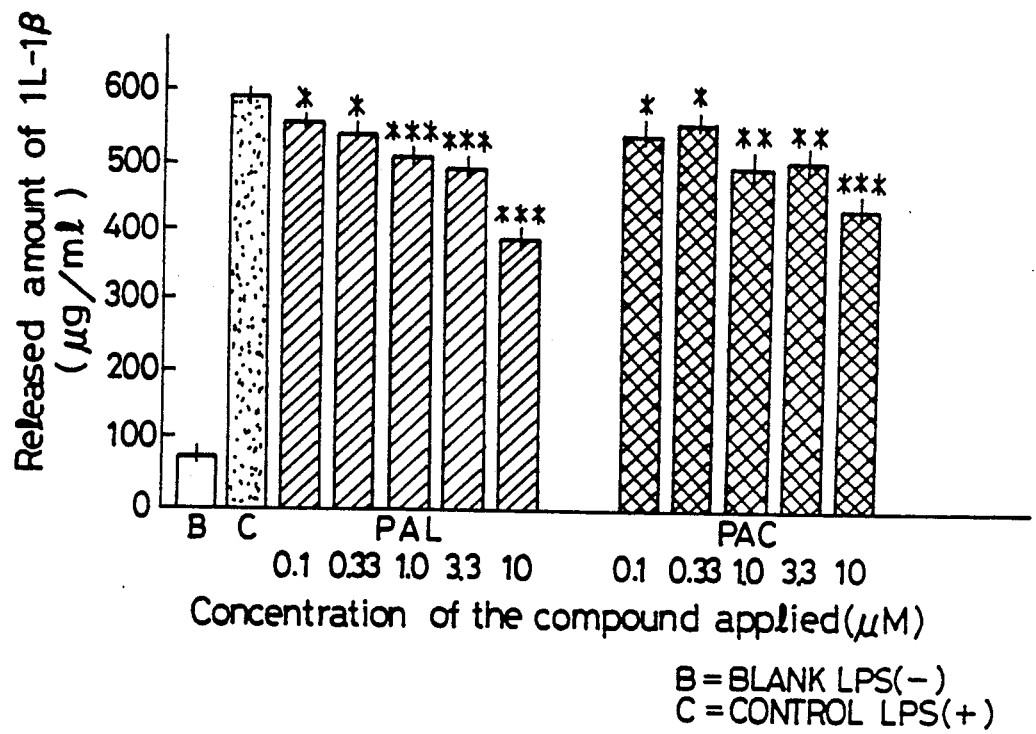

(ii) Inhibiting activity of the compound of the present invention on a release of IL-1 from human monocyte Monocyte were isolated from human venous blood by density-gradient centrifugation using a Ficoll-paque solution and obtained the cells having a purity of not less than 95% by purifying with a monocyte-separating plate. After dispersing the cells in a medium, RPMI 1640, containing 10% of FBS, the monocyte were inoculated in a culture dish in a ratio of $10^6$ cells/3 ml/well and cultured under an atmosphere containing 5% $CO_2$ at 37° C. for 30 minutes. Then, each 15 $\mu$l of DMSO solution of one of ACP, PAL and PAC was added to each well (a final DMSO concentration of 0.5%) and 30 minutes later a lipopolysaccharide (hereinafter referred to as "LPS"), a substance to stimulate IL-1 production, was added at a final LPS concentration of 10 $\mu$g/ml and they were cultured for 42 hours. Then, the reacted culture medium was recovered and accompanied cells with the medium were separated by centrifugation and obtained the supernatant free of cell. IL-1$\alpha$ and IL-1$\beta$ released from the cells were measured by ELISA method in the same manner as in item (i) above. As are shown in FIGS. 2(a) and 2(b), ACP, PAL and PAC significantly inhibit the release of IL-1 at concentration of 0.67, 0.33 and 10 $\mu$M, respectively.

As is shown in FIG. 2(c) at the right end, 3,4-di-n-propionyloxy-benzylidene di-n-propionate [indicated as ①], 3,4-di-n-dodecanoyloxy-benzylidene di-n-dodecanoate [indicated as ②], 3,4-di-n-octadecanoyloxy-benzylidene di-n-octadecanoate [indicated as ③] and 3,4-dibenzoyloxy-benzylidene di-benzoate [indicated as ④] also significantly inhibit the IL-1 release at the concentration of 3.3 $\mu$M.

Further, the following compounds,
3,4-di-n-butyryloxy-benzylidene di-n-butyrate,
3,4-di-n-tetradecanoyloxy-benzylidene di-n-tetradecanoate,
3,4-di-n-hexadecanoyloxy-benzylidene di-n-hexadecanoate,
3,4-diacetoxybenzylidene di-n-octadecanoate,
3,4-di-n-octadecanoyloxy-benzylidene diacetate,
3,4-diacetoxybenzaldehyde,
3,4-di-n-octadecanoylxybenzaldehyde,
3,4-dibenzoyloxybenzaldehyde,
3,4-diacetoxybenzoic acid and its sodium salt, and sodium salt of PAC
were also observed to have the similar activity.

(iii) Inhibiting activity on IL-1 release from cultured cartilage cells

Figure 3:
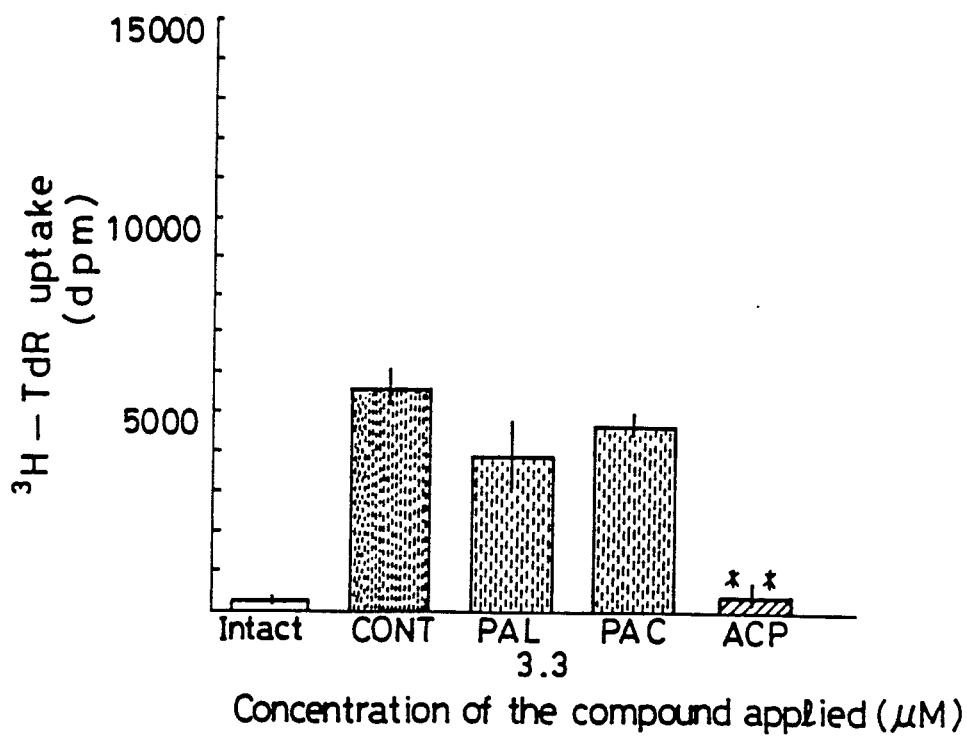
FIG. 3 shows the experimental results of the inhibiting effects of ACP, PAL and PAC on IL-1 release from cultured human cartilage cells. The values are shown in the form of a mean value ± standard error (n=3) on bar graphs.

Cartilages were aseptically taken out from knee and shoulder joints of young rabbit, treated with a Ham medium containing 0.2% collagenase and separated each other into single cells. After washed two times with a Ham medium containing 10% FBS, the cells were dispersed into the Ham medium containing 10% FBS at a concentration of $10^5$ cells/ml. Each DMSO solution containing one of PAL, PAC and ACP was added to the well to a final concentration of each compound of 3.3 μM (corresponding to a final DMSO concentration of 0.25%) and then 0.1 μg/ml of TPA and 0.2 μg/ml of $Ca^{2+}$ ionophore A 23187 were added to stimulate the release of IL-1 from the cartilage cells. After 24 hours of cultivation, IL-1 released into each of the supernatants was measured by a bioassay applying an incorporated amount of $^3H$-thymidine ($^3H$-TdR) as an index. As are shown in FIG. 3, all PAL, PAC and ACP inhibit the release of IL-1 from the cartilage cells. In the Figure, "Intact" means a case TPA and the ionophore were not added and accordingly no stimulation of IL-1 release was given.

Figure 4:
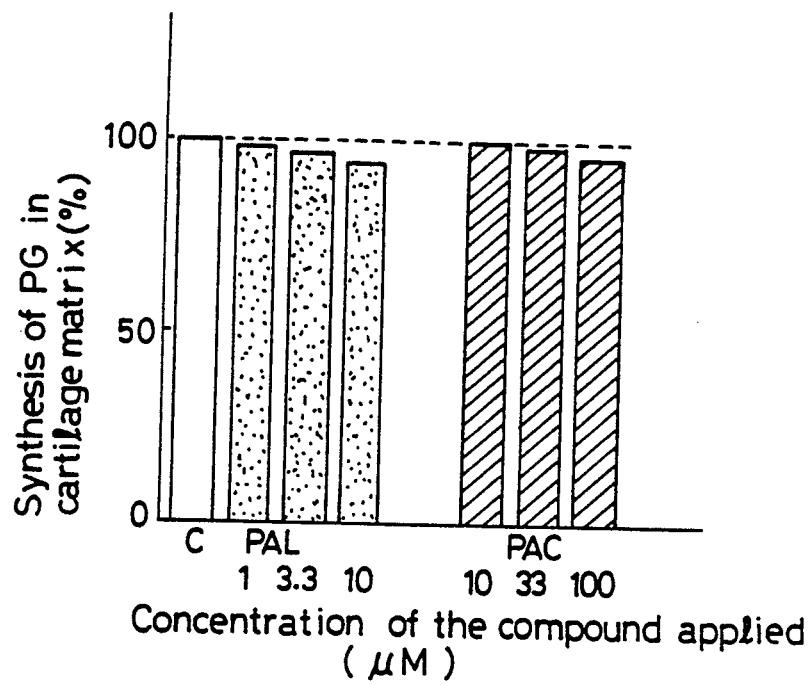
FIGS. 4(a), 4(b) and 4(c) show the experimental results of the inhibiting effects of PAL and PAC on synthesis, release and remaining ratios of proteoglycan in or from cartilage matrix.
Figure 4:
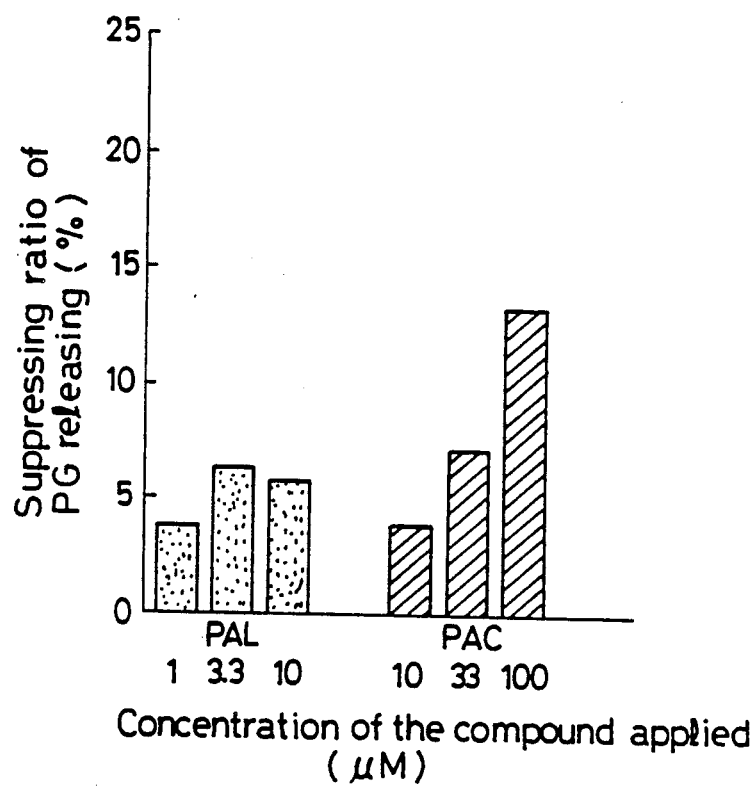
Figure 4C:
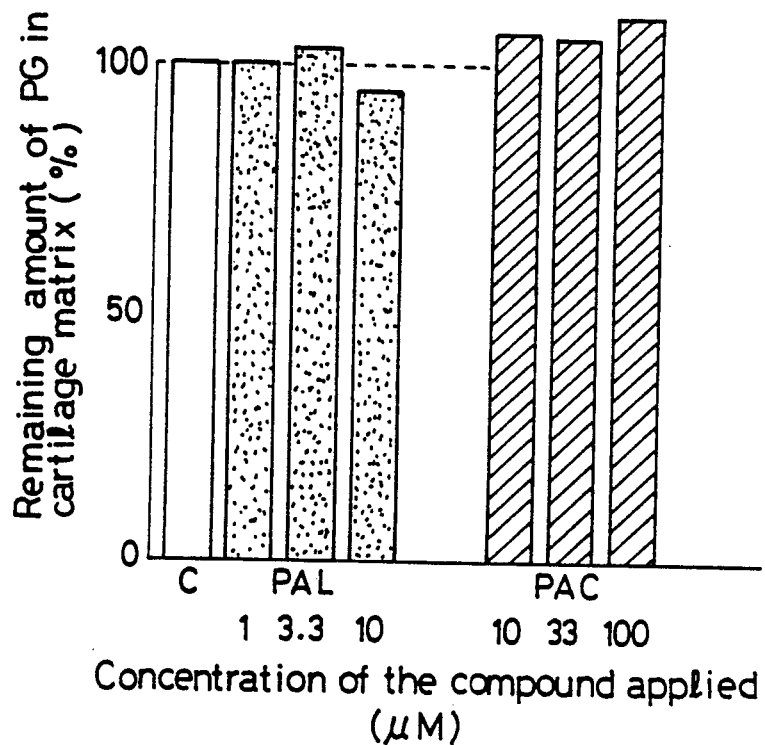

(3) Inhibition on release of proteoglycan (hereinafter referred to as "PG") from cultured cartilage cells Costal cartilage was aseptically taken out from male SD rats of 4 weeks age, enzymatically treated to separate it into single cells, then inoculated into a 12-well culture dish and cultured under an atmosphere containing 5% $CO_2$ at 37° C. After the chondrocytes had been grown to confluence, 1 to 10 μM of PAL or 10 to 100 μM of PAC was added and three hours later, 2 μ$C_i$ of $Na_2^{35}SO_4$ was further added to each well. Twenty four hours later, the synthesis amount in, release amount from and remaining amount of PG in the matrix were determined using amount of $^{35}S$ as an index. As are shown in FIGS. 4(a) and 4(b), no effect of each compound on the PG synthesis was observed and both PAL and PAC exhibited inhibiting activities on the PG release. In the Figures, the PG release in the control was defined as 100%. The remaining amount of PG in the matrix increased in proportion to the adding amount of PAL and PAC between the concentration of 1 and 3.3 μM and 10 and 100 μM, respectively [FIG. 4(c)]. ACP showed the effect having similar tendency as described above. In FIGS. 4(a), 4(b) and 4(c), the released amount of PG means the amount representing the PG degraded in and released from cartilage matrixes, which was calculated on a basis of $^{35}S$ in the culture medium. The remaining amount of PG means the PG not degraded in the matrixes and was also calculated in the same way as above. Sum of the released and the remaining amounts of PG is thought to be a synthesized PG. Accordingly, the more remaining amount and the less released amount of PG mean the compound has the more chondroprotective effect against osteoarthritis.

Figure 5:
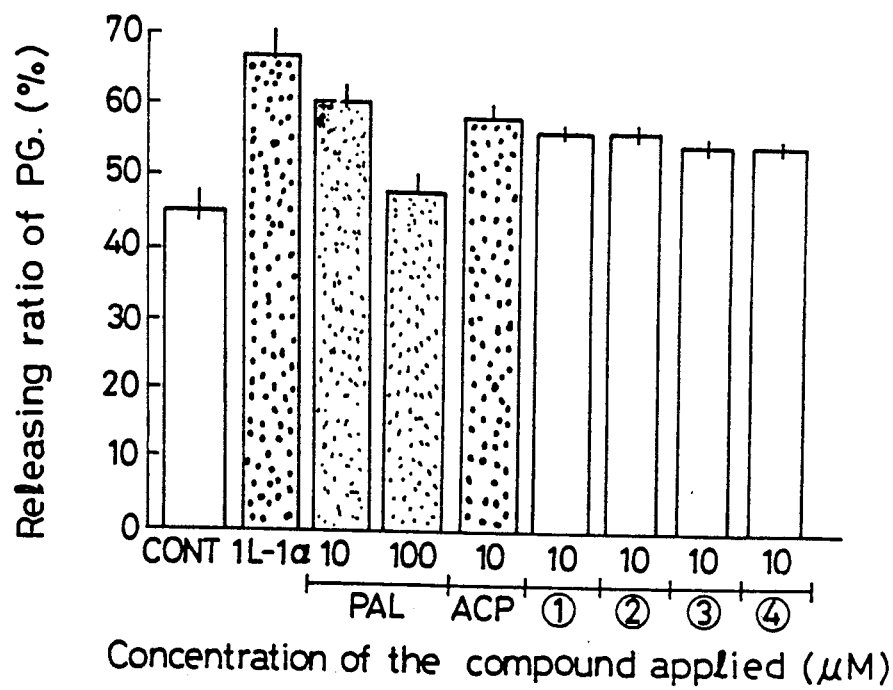
FIG. 5 shows the experimental results of the inhibiting effects of PAL, ACP, 3,4-di-n-propionyloxybenzylidene di-n-propionate, 3,4-di-n-dodecanoyloxybenzylidene di-n-dodecanoate, 3,4-di-n-octadecanoyloxybenzylidene di-n-octadecanoate and 3,4-dibenzoyloxybenzylidene dibenzoate, on proteoglycan release under an existence of IL-1α. The values are shown in the form of a mean value ± standard deviation (n=3) on bar graph.

Further, to a cultured cartilage matrix, in which PG is prelabelled in advance with 1 μ$C_i$ of $Na_2^{35}SO_4$, 20 units of IL-1α was added to each group including control group and 10 μM of PAL, 100 μM of PAL or 10 μM of ACP was added to each test group and studied the effect of each compound to the PG release from the cells. As are seen in FIG. 5, the addition of IL-1α increased a release of PG about 20% when compared to a control group (without an addition of IL-1) taking the prelabelled amount of $^{35}S$ as 100%. Further, PAL inhibited the release amount proportionally to the amount added and ACP also inhibited the release amount.

As also can be seen in FIG. 5, 10 μM of each of 3,4-di-n-propionyloxybenzylidene di-n-propionate [indicated as ①], 3,4-di-n-dodecanoyloxybenzylidene di-n-dodecanoate [indicated as ②], 3,4-di-n-octadecanoyloxybenzylidene di-n-octadecanoate [indicated as ③], 3,4-dibenzoyloxybenzylidene dibenzoate [indicated as ④], inhibited the release amount of PG.

The inhibiting activity of each of;
3,4-di-n-butyryloxybenzylidene di-n-butyrate,
3,4-di-n-tetradecanoyloxybenzylidene di-n-tetradecanoate,
3,4-di-n-hexadecanoyloxybenzylidene di-n-hexadecanoate,
3,4-diacetoxybenzylidene di-n-octadecanoate,
3,4-di-n-octadecanoyloxybenzylidene diacetate,
3,4-diacetoxybenzaldehyde,
3,4-di-n-octadecanoyloxybenzaldehyde,
3,4-dibenzoyloxybenzaldehyde,
3,4-diacetoxybenzoic acid and its sodium salt, and
PAC and its sodium salt, were also studied and gave the same effects.

As described above, the compound of the present invention demonstrated an excellent inhibiting activity against IL-1 production and release together with the inhibiting activity against PG release from cartilage cells so that the derivatives can show the protective action for joint cartilage with low toxicity (side effect). Accordingly the compound of the present invention are extremely useful as therapeutic agents for osteoarthritis, including osteogonarthritis, osteoanconitis, malum coxae deformans, spondylosis deformans.

Preparation of the pharmaceutical composition containing a compound of the present invention, as an active ingredient, for treating osteoarthritis are explained in the following Examples.

The compounds according to the present invention can be used in a variety of forms. The compounds of the present invention can be used singly and also with pharmaceutically acceptable diluents or other agents.

Among the compounds of the present invention, aldehyde derivatives are often stimulative to a living body and easily oxidized. To improve these defects, it is useful to make clathrate compounds of the derivative by reacting with cyclodextrin, etc. or to use them as a mixture with various amines, amino acids or saccharides.

The compounds of the present invention can be administered orally or parenterally and therefore can take any forms appropriate for such administration. The present compounds can also be administered in a wide variety of dosage forms, such as powders, granules, tablets, sugar coated tablets, capsules, suppositories, suspensions, liquids, emulsions, injections, ointments, etc, as far as contain a physiologically effective amount of the compound.

Therefore, a pharmaceutical composition containing the compound of the present invention, as an active ingredient, can be prepared by any publicly known methods. The content of the compound of the present invention in the pharmaceutical composition, as an active ingredient, can be widely adjusted from 0.01 to 100%, preferably 0.1 to 70% by weight.

The compounds of the present invention can be administered to humans and animals orally or parenterally. The oral administration include sublingual and the parenteral administration can include subcutaneous, intramuscular, intra-joint cavity, intravenous injections and infusions together with transdermal administration.

The dose amount of the compound of the present invention depends on the subject species such as animals and humans, the age, the individual difference, the stage of disorders and therefore, the dose exceeding the following dose range may be sometimes needed. However, generally speaking, the compound of the present invention can be administered orally to humans at a dose in a range of 0.1 to 500 mg/kg.body weight/day, preferably from 0.5 to 200 mg/kg.body weight/day, and parenterally, it can be administered at a dose in a range of 0.01 to 200 mg/kg.body weight/day, preferably from 0.1 to 100 mg/kg. body weight/day. Further, it is preferable to administer once to 4 times a day.

The preparation of the pharmaceutical composition containing the compound of the present invention, as an active ingredient is described in the following Examples. The part shown in the Examples expresses a part by weight, as long as not differently described.

EXAMPLE 1

Granules

| | |
|---|---|
| ACP | 71 parts |
| Lactose | 17 parts |
| Hydroxypropylcellulose having a low subsitution. | 10 parts |
| Hydroxypropylcellulose | 2 parts |

The above components were throughly mixed and kneaded using 32 parts of ethanol as an emollient, wet-granulated and dried to obtain the granules.

EXAMPLE 2

Tablets

To the granules prepared in the Example 1, 1% by weight of magnesium stearate was added and mixed well and the mixture was compressed and molded into the tablets.

EXAMPLE 3

Encapsulated drug

| | |
|---|---|
| PAL | 40 parts |
| Lactose | 50 parts |
| Hydroxypropylcellulose having a low substitution | 10 parts |

The above components were mixed well into homogenous powder and was packed in capsules to obtain the encapsulated drug.

EXAMPLE 4

Encapsulated drug

The drug was prepared in the same manner as in Example 3, using PAC instead of PAL.

EXAMPLE 5

Injection

| | |
|---|---|
| PAL | 1 part |
| Isotonic sodium chloride solution | 99 parts |

The above components were mixed under heating and sterilized to have the injection.

EXAMPLE 6

Injection

The injection was prepared in the same manner as in Example 5, using PAC instead of PAL.

EXAMPLE 7

Ointment

| | |
|---|---|
| 3,4-Di-n-propionyloxybenzylidene di-n-propionate | 5 parts |
| Purified lanolin | 4 parts |
| White bee wax | 4 parts |
| White vaseline | 87 parts |

The above components were kneaded well to give the ointment.

What is claimed is:

1. A method for treating a patient suffering from osteoarthritis comprising administering a physiologically effective amount of pharmaceutical composition containing at least one compound, as an active ingredient, represented by the formula (I):

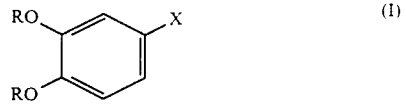

wherein R represents a hydrogen atom or an acyl group; X represents a CHO group, a COOH group, a physiologically acceptable salt thereof or a $CH(OR')_2$ group wherein R' represents an acyl group.

2. The method according to claim 1, wherein said R and R' represent the same acyl group.

3. The method according to claim 1, wherein said R and R' independently represents different acyl group.

4. The method according to claim 1, wherein said R and R' respectively represent

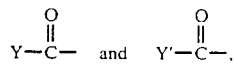

wherein Y and Y' independently represents a straight chain alkyl group having 1 to 18 carbon atoms or an aromatic residue.

5. The method according to claim 1, wherein said R and R' respectively represents

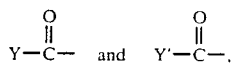

wherein Y and Y' independently represents a branched chain alkyl group having 1 to 18 carbon atoms.

6. The method according to claim 1, wherein said pharmaceutically acceptable salt is a sodium salt.

7. The method according to claim 1, wherein said compound is 3,4-dialkanoyloxybenzylidene dialkanoate.

8. The method according to claim 1, wherein said compound is 3,4-dihydroxybenzaldehyde.

9. The method according to claim 1, wherein said compound is 3,4-dihydroxybenzoic acid and a physiologically acceptable salt thereof.

* * * * *